(12) United States Patent
Hossainy et al.

(10) Patent No.: US 8,021,678 B2
(45) Date of Patent: Sep. 20, 2011

(54) IMPLANTABLE MEDICAL DEVICE WITH POLYMER COATING IN A SURFACE AREA TO VOLUME RATIO PROVIDING SURFACE EROSION CHARACTERISTICS

(75) Inventors: Syed Faiyaz Ahmed Hossainy, Fremont, CA (US); Stephen D. Pacetti, San Jose, CA (US); Murthy V. Simhambhatla, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1624 days.

(21) Appl. No.: 11/351,598

(22) Filed: Feb. 10, 2006

(65) Prior Publication Data

US 2007/0190103 A1    Aug. 16, 2007

(51) Int. Cl.
*A61F 2/02*    (2006.01)
(52) U.S. Cl. .................................................. 424/426
(58) Field of Classification Search .................. None
See application file for complete search history.

(56) References Cited

U.S. PATENT DOCUMENTS 5,696,175 A      12/1997  Mikos et al.
6,926,919 B1 *   8/2005   Hossainy et al. ............ 427/2.25

FOREIGN PATENT DOCUMENTS

| WO | WO 2005/059003 | 6/2005 |
| WO | WO 2005/063319 | 7/2005 |
| WO | WO 2006/023672 | 3/2006 |

OTHER PUBLICATIONS

Grube et al, Rapamycin analogs for Stent based Local Drug Delivery, Herz, pp. 162-166, vol. 29, No. 2,, Mar. 2004.*
"Peripheral Vascular Disease", www.americanheart.org/presenter.jhtml?identifier=4692, Dec. 9, 2005, 2 pgs.
"Peripheral Artery Disease", www.americanheart.org/presenter.jhtml?identifier=3020242, Dec. 9, 2005, 1 pg.
"Coronary Artery Disease", www.nhlbi.nih.gov/health/dci/Diseases/Cad/CAD_Causes.html, Dec. 9, 2005, 1 pg.
"Carotid Artery Disease", www.clevelandclinic.org/heartcenter/pub/guide/disease/vascular, Dec. 9, 2005, 3 pgs.
Lisa Brannon-Peppas, "Polymers in Controlled Drug Delivery", www.devicelink.com/mpb/archive/97/11/003.html, Dec. 11, 2005, 14 pgs.
"Coronary Artery Disease", womentshelth.gov, www.4woman.gov/faq/coronary.htm, Dec. 9, 2005, 5 pgs.
International Search Report for PCT/US2007/002126, filed Jan. 26, 2007, mailed Nov. 19, 2007, 14 pgs.

* cited by examiner

*Primary Examiner* — Carlos Azpuru
(74) *Attorney, Agent, or Firm* — Squire, Sanders & Dempsey (US) LLP

(57) ABSTRACT

The present invention relates to an implantable medical device comprising therapeutic agents coated on the device using polyesters for the drug reservoir layer that exhibit surface-eroding characteristics.

36 Claims, No Drawings

IMPLANTABLE MEDICAL DEVICE WITH POLYMER COATING IN A SURFACE AREA TO VOLUME RATIO PROVIDING SURFACE EROSION CHARACTERISTICS

FIELD

This invention relates to the fields of polymer chemistry, medicinal chemistry, materials science and medical devices.

BACKGROUND

The discussion that follows is intended solely as background information to assist in the understanding of this invention; nothing in this section is intended to be, nor is it to be construed as, prior art to the invention.

In the early 1980's, the utility of implantable medical devices, which had been in use by the medical community for about 30 years, was expanded to include localized delivery of drugs. It was found that implantable devices could be fabricated with drugs incorporated directly into their structure or, more commonly, incorporated in a coating adhered to a surface of the device. In either case, the drug was shielded from the environment until the device was delivered to and released at the treatment site. The advantages of localized drug delivery are manifest.

Site specific delivery permits the establishment of a high local concentration of a drug with concomitant low level systemic exposure and less potential for undesirable side effects. Thus, for example, the hemorrhagic complications that can accompany systemic delivery of an antithrombotic agent can be avoided. Likewise, the pervasive toxicity of antineoplastics to all living cells can be focused on malignant cells only by delivery of the drug at or into a tumor. Localized delivery also permits use of drugs that, for one reason or another, are not amenable to delivery by other means. This includes drugs that, for instance, are susceptible to degradation under physiological conditions and therefore would biodegrade before reaching the treatment site if administered systemically and drugs that are substantially insoluble in physiological solution, which is primarily aqueous, such that they precipitate and are immobilized almost immediately on administration.

Of course, the ability to use less of a drug using localized delivery can also constitute a substantial economic benefit.

One technique for the localized delivery of drugs involves dispersion of the drug in a polymeric carrier to create a "drug reservoir" from which the drug can be delivered once situated at a treatment site. A drug reservoir polymer must be biocompatible, that is, its intact, as-synthesized state and its degradation products, if it decomposes to any substantial degree, must not be, or at least should minimally be, toxic or otherwise injurious to living tissue. Furthermore, the polymer or its degradation products should not, or again should at least minimally and/or controllably, cause an immunological reaction in living tissue.

An area of on-going research regarding localized drug delivery is control of a drug release profile. The physical and chemical properties of the polymer employed as the drug reservoir in large part controls the release profile of a drug dispersed in it. For instance, if the drug reservoir polymer is durable, that is if it is stable in a physiological environment and does not biodegrade to any substantial degree, then the predominant mechanism by which a drug will escape the reservoir is by simple passive diffusion from the polymer matrix, with or without prior swelling of the polymer due to exposure to bodily fluids. The drug release profile achieved by passive diffusion may not, however, be optimal. Conditions such as whether or not the reservoir polymer is cross-linked, and if so the structure of the cross-linked matrix, in particular the size of pores and the tortuousness of the path the drug must take to arrive at the surface of the polymer will affect the release profile. The physical dimensions of the drug itself, as well the geometry of the implantable device and the geometry of the reservoir layer will also impact the release profile. For example, release from a thin layer of polymer coated on a device may differ substantially from the release from microspheres or nanospheres adhered to the surface of the device. The thickness or, in the case of a sphere, the average diameter, of the reservoir will also affect drug release.

An alternative to using durable polymers as the drug reservoir is using biodegradable polymers. While a host of parameters such as molecular weight, molecular weight distribution, sterilization history, shape, annealing, processing conditions, presence of ionic groups, configurational structure, etc, contribute to determining a polymeros degradation characteristics, a primary factor that determines biodegradability is chemical composition. That is, biodegradable polymers have functional linking groups bonding the monomers together that are selected so as to be susceptible to biodegradation in vivo. The degradation is often enzyme-catalyzed, but may also be affected by other physiological factors such as pH. Biodegradable polymers can be divided into two general types, surface-eroding and bulk-eroding.

Surface-eroding polymers tend to be hydrophobic, causing mass loss at the polymer surface to be greater than mass loss caused by ingress of water into the polymer bulk. Surface erosion generally occurs at a controlled, predictable rate. Thus, a drug contained within the polymer matrix is released at a constant rate as erosion progresses, provided that the exposed surface area of the polymer does not change. Surface-eroding polymers include polyanhydrides, polyorthoesters and polyketals. With the exception of polyketals, the degradation products of these polymers include acids. Since this degradation can be acid-catalyzed as well an enzyme-catalyzed, auto-catalysis may occur.

Autocatalysis occurs when the degradation products of a polymer themselves are capable of catalyzing further degradation of the polymer. The subsequent build-up of more and more catalyst causes an escalating degradation rate. In the case of surface-eroding polymers, however, the phenomenon does not usually occur because the acidic degradation products are rapidly washed away from the surface of the polymer and are not present in high enough concentration to substantially autocatalyze further degradation.

The degradation products of surface-eroding polymers, like any polymer intended for use in vivo, must be biocompatible. While a number of such polymers are known and have found use in implantable medical devices used for the controlled drug release of therapeutic agents, in general their degradation products are rarely totally innocuous and their use must generally be carefully monitored.

On the other hand, polylactides, polyglycolides and co-polymers thereof are largely innocuous in vivo. They have been used in vivo for over 20 years beginning with biodegradable sutures. Their popularity stems from the fact that their degradation products, lactic acid and glycolic acid, are naturally-occurring compounds that, upon formation in vivo, are capable of entering into the Krebs cycle and thereafter being converted to carbon dioxide and water. Thus, these polymer and their degradation products place little or no additional stress on a patient's often already compromised physiological state. Polylactides and polyglycolides are, however, bulk-eroding polymers.

Bulk-eroding biodegradable polymers tend to be hydrophilic, that is, water compatible. These water compatible polymers absorb water and along with it the enzymes and other biodegradation-causing components of a physiological system. The absorbed components cause internal degradation of the polymer at a rate that competes with the rate of surface erosion. That is, degradation takes place simultaneously throughout the polymer matrix. The result can be an extremely complex drug release profile as differential degradation takes place in the bulk of the polymer and drug is released from throughout the polymer matrix in a haphazard manner. Rather than a smooth, linear release profile such as that obtained with surface-eroding polymers, burst releases of massive amounts of drug, which can be detrimental to the health and safety of the patient, may occur. Autocatalysis compounds this situation for polyesters such as polylactides and polyglycolides. Unlike surface-eroding polymers, when bulk-eroding polymers degrade to their component acids, the acids remain trapped for an extended period of time within the remaining polymer matrix wherein they catalyze further degradation, which further complicates the release profile of an incorporated therapeutic agent.

A method of manipulating bulk-eroding polymers such that in use they exhibit surface erosion characteristics rather than bulk erosion characteristics would be desirable. The present invention provides such a method.

SUMMARY

Thus, in one aspect the present invention relates to an implantable medical device, comprising:
a polymer layer comprising a biocompatible biodegradable polymer wherein the polymer layer is disposed over a surface of the medical device at a surface area to volume ratio of from about 100 $mm^{-1}$ to about 1000 $mm^{-1}$; and, comprising a therapeutic agent dispersed in the polymer layer at a drug/polymer wt/wt ratio of from about 1:5 to about 5:1.

In an aspect of this invention, the surface is an outer surface and optionally all or part of an edge surface.

In an aspect of this invention, the surface is a luminal surface and optionally all or part of an edge surface.

In an aspect of this invention, the polymer layer has a surface-area-to-volume ratio of from about 100 $mm^{-1}$ to about 500 $mm^{-1}$.

In an aspect of this invention, the polymer layer has a surface area to volume ratio of from about 100 $mm^{-1}$ to about 250 $mm^{-1}$.

In an aspect of this invention, the drug/polymer wt/wt ratio is from about 1:2 to 2:1.

In an aspect of this invention, the drug/polymer wt/wt ratio is about 1:1.

In an aspect of this invention, the biocompatible biodegradable polymer is selected from the group consisting of poly(L-lactide), poly(D-lactide), poly(D,L-lactide), poly(meso-lactide), polyglycolide, poly(L-lactide-co-glycolide), poly(D-lactide-co-glycolide), poly(L-lactide-co-D,L-lactide), poly(D,L-lactide-co-glycolide), poly(meso-lactide-co-glycolide), poly(caprolactone), poly(hydroxyvalerate), poly(hydroxybutyrate) and poly(ethylene glycol-co-butylene terephthalate) (POLYACTIVE®), poly(ester amide).

In an aspect of this invention, the biocompatible biodegradable polymer has a molecular weight of from about 20 to about 600 kDaltons.

In an aspect of this invention, the biocompatible biodegradable polymer has as molecular weight of from about 40 to about 200 kDaltons.

In and aspect of this invention, the biocompatible biodegradable polymer has as molecular weight of from about 50 to about 70 kDaltons.

In an aspect of this invention, the biocompatible biodegradable polymer is substantially amorphous.

In an aspect of this invention, the amorphous biocompatible biodegradable polymer is selected from the group consisting of poly(D,L-lactide), poly(meso-lactide), poly(L-lactide-co-glycolide), poly(D-lactide-co-glycolide)-poly(D,L-lactide-co-glycolide), poly(L-lactide-co-D,L-lactide), and poly(meso-lactide-co-glycolide).

In an aspect of this invention, the therapeutic agent is selected from the group consisting of actinomycin D, paclitaxel, docetaxel, methotrexate, azathioprine, vincristine, vinblastine, fluorouracil, doxorubicin hydrochloride, mitomycin, sodium heparin, low molecular weight heparins, heparinoids, heparin derivatives having hydrophobic counter ions, hirudin, argatroban, forskolin, vapiprost, prostacyclin, dextran, D-phe-pro-arg-chloromethylketone, dipyridamole, glycoprotein IIb/IIIa platelet membrane receptor antagonist antibody, recombinant hirudin, and thrombin, angiopeptin, captopril, cilazapril, lisinopril, nifedipine, colchicine, fibroblast growth factor (FGF) antagonists, fish oil (ù-3-fatty acid), histamine antagonists, lovastatin, monoclonal antibodies, nitroprusside, phosphodiesterase inhibitors, prostaglandin inhibitors, suramin, serotonin blockers, steroids, thioprotease inhibitors, triazolopyrimidine, nitric oxide, permirolast potassium, alpha-interferon, genetically-engineered epithelial cells, rapamycin, everolimus, biolimus, dexamethasone and 17-allylamino-17-demethoxygeldanamycin.

In an aspect of this invention, the therapeutic agent is an antiproliferative agent.

In an aspect of this invention, the therapeutic agent is everolimus.

In an aspect of this invention, the therapeutic agent is 17-allyoamino-17-demethoxygeldanamycin.

In an aspect of this invention, the implantable medical device further comprises a primer layer applied onto the surface of the device between the surface and the polymer layer.

In an aspect of this invention, the primer layer comprises a polymer selected from the group consisting of poly(monochloro-paraxylylene) (PARYLENE C®), polyacrylate, poly(n-butylmethacrylate), polymethacrylate, poly(D,L-lactide), poly(L-lactide), poly(L-lactide-co-glycolide), poly(meso-lactide), poly(meso-lactide-co-glycolide), poly(D,L-lactide-co-glycolide), poly(caprolactone), poly(hydroxyvalerate) poly(hydroxybutyrate) and poly(ethylene glycol-co-butylene terephthalate) (POLYACTIVE®), poly(ester amide).

In an aspect of this invention, the primer layer comprises a polymer selected from the group consisting of poly(n-butyl methacrylate) and PARYLENE C®.

An aspect of this invention is a method of treating a vascular disease comprising:
deploying to a site in the vasculature of a patient in need thereof an implantable medical device comprising a biocompatible biodegradable polymer layer disposed over a surface thereof such that the surface area to volume ratio is from about 100 $mm^{-1}$ to about 1000 $mm^{-1}$, the polymer layer further comprising a therapeutic agent in a drug/polymer wt/wt ratio of from about 1:5 to about 5:1; and,
positioning the implantable medical device at the site.

In an aspect of this invention, deploying in the above method comprises using a catheter.

In an aspect of the above method, the drug/polymer wt/wt ratio is from about 1:2 to about 2:1.

In an aspect of the above method, the drug/polymer wt/wt ratio is about 1:1.

In an aspect of the above method, the biocompatible biodegradable polymer has a number average molecular weight of from about 20 kDa to about 600 kDa.

In an aspect of the above method, the biocompatible biodegradable polymer has a number average molecular weight of from about 40 kDa to about 200 kDa.

In an aspect of the above method, the number average molecular weight is from about 50 kDa to about 100 kDa.

In an aspect of the above method, the biocompatible biodegradable polymer is selected from the group consisting of poly(L-lactide), poly(D-lactide), poly(D,L-lactide), poly(meso-lactide), poly(L-lactide-co-D,L-lactide), polyglycolide, poly(L-lactide-co-glycol ide), poly(D-lactide-co-glycolide), poly(D,L-lactide-co-glycolide), poly(meso-lactide-co-glycolide), poly(caprolactone), poly(hydroxyvalerate), poly(hydroxybutyrate) and poly(ethylene glycol-co-butylene terephthalate) (POLYACTIVE®), poly(ester amide).

In an aspect of the above method, the biocompatible biodegradable polymer is substantially amorphous.

In an aspect of the above method, the amorphous, biocompatible biodegradable polymer is selected from the group consisting of poly(D,L-lactide), poly(meso-lactide), poly(L-lactide-co-D, L-lactide), poly(L-lactide-co-glycol ide), poly(D,L-lactide-co-glycolide), poly(D-lactide-co-glycolide) and poly(meso-lactide-co-glycolide).

In an aspect of the above method, the vascular disease is restenosis.

In an aspect of the above method, the vascular disease is vulnerable plaque.

In an aspect of the above method, the therapeutic agent is selected from the group consisting of everolimus and 17-allylamino-17-demethoxy-geldanamycin.

DETAILED DESCRIPTION

Definitions

As used herein, use of the singular includes the plural unless expressly stated otherwise. That is, "a" and "the" may refer to one or to a plurality of whatever is modified by the word. For example, a "pharmaceutical agent" includes one such agent or two or more such agents. Likewise, "a polymer" or "the polymer" may refer to one polymer or to a plurality of polymers.

As used herein, the terms "about" or "approximately" mean that the parameter so modified need not be exactly the value or range of values stated herein to still come within the scope of this invention. While circumstances and the knowledge of those skilled in the art may require an even greater departure from the indicated value or range of values, at a minimum "about" or "approximately" is to be construed to be at least ±15% of the value so modified, in some embodiments at least plus or minus 5% of the value.

As used herein, "optional" or "optionally" when used to modify an element of this invention means that the element may be present or it may not be present and both are within the ambit of this invention.

As used herein, "biodegradable" refers to the in vivo cleaving of bonds in a polymer chain that link the monomer-derived portions together resulting in the break-down of the polymer into smaller and smaller fragments until the fragments are small enough to be either absorbed and metabolized or excreted by the organism. The primary mechanism of biodegradation for some embodiments of this invention is enzyme-catalyzed hydrolysis of ester groups.

As used herein, "biocompatible" refers to an intact polymer and to its biodegradation products all of which are not, or at least are minimally, toxic to living tissue; do not, or at least minimally and reversibly, injure living tissue; and/or do not, or at least minimally and/or controllably, cause an immunological reaction in living tissue.

As used herein, the "vascular system" refers to the arteries, veins and capillaries that transport blood throughout the body. This includes, without limitation, the cardiovascular system, the carotid artery system, the peripheral vascular system and the veins that complete the circulatory system between each of the foregoing and the heart. The cardiovascular system is the general circulatory system between the heart and all parts of the body. The carotid system supplies blood to the brain. The peripheral vascular system carries blood to and from the peripheral organs such as, without limitation, the arms, legs, kidneys and liver.

As used herein, "vascular disease" refers to coronary artery diseases or disorders, carotid artery diseases or disorders and/or peripheral artery diseases or disorders such as known or become known in the art.

In particular, at present, the implantable medical device of this invention may be used to treat or prevent atherosclerosis, restenosis and vulnerable plaque.

Atherosclerosis is a disease of the arterial intima wherein the formation of fibrous plaques resulting from the deposition of fatty substances, cholesterol, cellular waste products and the like in the inner lining of an artery leads to stenosis/occlusion of the lumen of the artery. The arteries of the brain, heart, kidneys and other vital organs as well as those of the arms and legs may be affected. Atherosclerosis of the arteries of the brain, in particular the carotid arteries, may result in a stroke while atherosclerosis of the arteries of the heart may lead to a myocardial infarction, i.e., a heart attack.

Restenosis refers to the re-narrowing or blockage of an artery (i.e., the recurrence of a stenosis) at the same site where angioplasty was previously performed. It is usually due to thrombosis and vascular injury accompanied by renewed smooth muscle cell proliferation. Prior to the advent of implantable stents to maintain the patency of vessels opened by angioplasty, restenosis occurred in 40-50% of patients within 3 to 6 months of undergoing the procedure. Post-angioplasty restenosis before stents was due primarily to neointimal hyperplasia at the site of the procedure. While stents have reduced the occurrence of restenosis substantially, they themselves are also susceptible to restenosis due to abnormal tissue growth at the site of implantation. This form of restenosis tends to also occur at 3 to 6 months after stent placement but it is not affected by the use of anti-clotting drugs. Rather, such drugs as sirolimus and more recently everolimus and 17-allylamino-17-demethoxygeldanamycin have been used or suggested for localized delivery at the site of stent placement to reduce the incidence of restenosis.

A vulnerable plaque refers to an atheromatous plaque that has a very thin wall separating a lipid-laden core from the lumen of an artery. The thinness of the wall renders the plaque susceptible or vulnerable to rupture. When the plaque ruptures, tissue factor, lipids and cholesterol crystals are exposed to the blood flow causing the formation of blood clots that may result in narrowing or complete blockage of the lumen. The debris is released into the arterial lumen and is transported by blood flow to other parts of the vasculature where the size of the debris particles causes them to be trapped at smaller vessels such as capillaries resulting in obstruction with potential serious consequences. Furthermore, rupture of an atheroma may result in bleeding from the lumen of the artery into the tissue of the atheroma resulting in an increase in size of the of the atheroma to the point that it may narrow or completely obstruct the lumen. In addition, the formation of blood clots at the site of atheroma rupture may itself result in narrowing or complete blockage of the lumen.

As used herein, "known or suspected" to be afflicted with a vascular disease refers to the degree of certainty of the existence of the disease in a patient. To be afflicted with a "known" disease means that diagnostic testing has revealed with reasonable certainty a particular vascular disease located in a reasonable well-defined region of a patient's vasculature. An example of such a vascular disease is, without limitation, restenosis, the diagnosis and location of which in a patient's vasculature is well-established in the art. An example of a "suspected" vascular disease is, without limitation, vulnerable plaque which is difficult to diagnose and/or to locate in a patient's vasculature. Such indicators as temperature differences in the afflicted region of the vasculature compared to unaffected regions have been explored for their diagnostic utility but at present no reasonably certain method of diagnosis and locating vulnerable plaque has been reported. It is relatively well established, however, that vulnerable plaque tends to appear most frequently in the first third of the main coronary arteries measuring distally from the coronary ostia.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants, prostheses, vascular grafts, self-expandable stents, balloon-expandable stents, stent-grafts, grafts, artificial heart valves and cerebrospinal fluid shunts. Of course, an implantable medical device specifically designed and intended solely for the localized delivery of a therapeutic agent is within the scope of this invention. The implantable medical device may be constructed of any biocompatible material capable of being coated with an adherent layer containing a therapeutic agent.

Implantable medical devices made of virtually any material, i.e., materials presently known to be useful for their manufacture and materials that may be found to be so in the future, may be used with a coating of this invention. For example, without limitation, an implantable medical device useful with this invention may be made of one or more biocompatible metals or alloys thereof including, but not limited to, cobalt-chromium alloy (ELGILOY, L-605), cobalt-nickel alloy (MP-35N), 316L stainless steel, high nitrogen stainless steel, e.g., BIODUR 108, nickel-titanium alloy (NITINOL), tantalum, platinum, platinum-iridium alloy, gold and combinations thereof.

Alternatively, the implantable medical device may be made of one or more biocompatible, durable polymers including, but not limited to, polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

A presently preferred implantable medical device is a stent. A stent refers generally to any device used to hold tissue in place in a patient's body. A subset of stents is those stents used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. A stent can be used to strengthen the wall of the vessel in the vicinity of a vulnerable plaque and act as a shield against such rupture. A stent can be used in, without limitation, neuro, carotid, coronary, pulmonary, aortic, renal, biliary, iliac, femoral and popliteal arteries as well as other regions of the vasculature. A stent can be used in the treatment or prevention of diseases or disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

A vascular stent may be formed by any of a number of well-known methods including the extrusion of a polymer into the shape of a tube. Pre-selected patterns of voids can then be formed into the tube in order to define a plurality of spines or struts that impart a degree of flexibility and expandability to the tube. Alternatively, the drug loaded polymer may be applied to the selected surfaces of a stent made of, for example, stainless steel. The stent can be, for example, immersed in the molten polymer or sprayed with a liquid or dissolved form of the polymer. Or a polymer may be extruded in the form of a tube, which is then co-drawn with a tube of stainless steel, or other suitable metallic materials or alloys. By co-drawing two tubes of the polymer with the metal tube, one positioned about the exterior of the metal tube and another positioned within the metal tube, a tube having multi-layered walls is formed. Subsequent perforation of the tube walls to define a pre-selected pattern of spines or struts imparts the desired flexibility and expandability to the tube to create a stent.

In addition to the above uses, stents may also be deployed for the localized delivery of therapeutic agents to specific treatment sites in a patient's body. In fact, therapeutic agent delivery may be the sole purpose of a stent or the stent may be primarily intended for another purpose such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. In any event, due to the expansion of the stent, any coating thereon must be flexible and capable of elongation. The polymeric coatings of this invention exhibit these characteristics.

As use herein, a "reservoir" or "reservoir layer" refers to a polymer that is disposed in a layer over a surface of an implantable medical device and that has dispersed within its three-dimensional structure a therapeutic agent that is released from the matrix into the surrounding environment once the device has been placed at a desired location in a patient's body. A reservoir may also refer to a stand-alone layer of a polymer in the form of a tape or the like wherein the tape has all the properties indicated herein for a coated layer. The tape will also exhibit biodegradation characteristics of a surface-eroding polymer even though it is constructed of a normally bulk-eroding polymer.

As used herein, "coating" refers to a single layer or to multiple layers of a substance or substances disposed over a surface of an implantable medical device. Thus, a reservoir layer alone may constitute a coating, as will a primer layer applied directly to the surface of an implantable medical device between a reservoir layer and the surface of the device and as will a topcoat disposed over the reservoir layer. A combination of any of the foregoing layers will likewise compose a coating. It will be readily apparent to those skilled in the art which meaning of coating is intended in any particular aspect of the invention described herein based on the context.

As used herein, a "surface" of an implantable medical device refers to an outer surface, that is a surface that is directly in contact with the external environment and/or an inner surface if the device comprises a lumen and/or the edge of the device that connects the outer surface with the lumen. Unless expressly stated to be otherwise, "surface" will refer to all or any combination of the preceding.

As used herein, to "dispose" a layer over a surface means to form a layer of a polymer over the surface of an implantable medical device or over the surface formed by a previously disposed layer. The layer can be formed by any means presently known or as such may become known in the future including at present, without limitation, spraying, dipping, electrodeposition, roll coating, brushing, direct droplet application and molding.

As used herein, to dispose a layer "over" a surface of a device or over the surface formed by a previously disposed layer refers to the application of the layer between the indicated surface and the external environment but not necessarily in direct contact with the indicated surface. That is, there may be one or more additional layers between the layer being disposed "over" the surface and the surface itself such as, without limitation, a spacing layer, a timing layer, etc.

In contrast to the above, "apply onto", and variations thereof, a surface refers to forming a layer of a polymer directly on and in contact with the indicated surface.

As used herein, "deploying" a device to a site in a patient's vasculature refers to the delivery of the device by any number of techniques well-known in the art. For example, without limitation, such a technique may involve appending the device to the distal end of a catheter, which is then introduced into the patient's vasculature at a remote entrance site such as, without limitation, the femoral artery if it is a cardiovascular artery that is being treated. The catheter is guided through the vasculature until the site known or suspected to be affected by the disease is reached. There, the implantable medical device is released from the distal end of the catheter, which is then withdrawn leaving the device implanted in the artery.

As used herein, a "surface area to volume" ratio refers to the result of the division of the surface area of a polymer layer in units of mm² divided by the volume of the layer, that is, the surface area multiplied by the thickness of the layer, in mm³. As used herein, "surface area" means that area that is exposed to the body or the external environment. The measurements are taken only after all solvents that may have been used in the coating process have been substantially removed from the layers. The resulting number has the units mm²/mm³ or 1/mm or mm$^{-1}$.

As used herein, "drug/polymer wt/wt ratio" is synonymous with and used interchangeably with "therapeutic agent/polymer wt/wt ratio" and refers to the gross weight of a therapeutic substance in a polymer layer coated on an implantable medical device divided by the gross weight of the polymer in the layer, each being expressed in the same units of measure.

As used herein, molecular weight as it pertains to a polymer refers to a number average molecular weight as determined using gel permeation chromatography.

As used herein, a "primer layer" refers to a polymeric layer applied directly to a surface of an implantable medical device to improve the adhesion of subsequently applied layers. Useful primers include polymers such as, without limitation, polyesteramides (PEAs), Parylene C®, polyacrylates and polymethacrylates (e.g., poly(buyl methacrylate).

As used herein, a "therapeutic agent" refers to a substance that, when administered to a patient, has a beneficial effect on the health and well-being of the patient. A therapeutic agent may be, without limitation, a small molecule drug, a large molecule drug, a radioisotope, a peptide, an antibody, a protein, an enzyme, an oligonucleotide, a DNA, an RNA, a liposome, a microparticle or nanoparticle that has encapsulated within it any of the foregoing or even a bare nanoparticle, which may comprise any of the foregoing agents. Alternatively, the therapeutic agents may be nanoparticulate as such may become available in the future.

Specific examples, without limitation, of therapeutic agents that may be used with the polymers of this invention include, without limitation, antiproliferative drugs such as actinomycin D, or derivatives or analogs thereof. Actinomycin D is also known as dactinomycin, actinomycin IV, actinomycin $I_1$, actinomycin $X_1$, and actinomycin $C_1$;

antineoplastics and/or antimitotics such as, without limitation, paclitaxel, docetaxel, methotrexate, azathioprine, vincristine, vinblastine, fluorouracil, doxorubicin hydrochloride, and mitomycin;

antiplatelet, anticoagulant, antifibrin, and antithrombin drugs such as, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin, and thrombin;

cytostatic or antiproliferative agents such as, without limitation, angiopeptin; angiotensin converting enzyme inhibitors such as captopril, cilazapril or lisinopril; calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide; antiallergic agent such as, without limitation, permirolast potassium; and, other therapeutic agents such as, without limitation, alpha-interferon, genetically engineered epithelial cells, tacrolimus, clobetasol, dexamethasone and its derivatives, and rapamycin, its derivatives and analogs such as 40-O-(2-hydroxyethyl)rapamycin (EVEROLIMUS®), 40-O-(3-hydroxypropyl)rapamycin, 40-O-[2-(2-hydroxyethoxy)]ethylrapamycin, 40-O-tetrazolylrapamycin and 17-allylamino-17-demethoxygeldanamycin and biolimus.

As used herein, "low molecular weight heparins" refers to fragments of unfractionated heparin. Whereas unfractionated heparin is a heterogeneous mixture of highly sulfated polysaccharide chains ranging in molecular weight from about 3,000 to about 30,000 DA, low molecular weight heparins have a molecular weight between about 4,000 and about 6,000 DA. The term "low molecular weight heparins" and the molecules to which the term refers are well-known to those skilled in the medical arts.

As used herein, "heparinoids" refers to naturally-occurring and synthetic highly sulfated polysaccharides that are structurally similar to heparin. Examples, without limitation, of heparinoids are danaparoid sodium, fondaparinux and idraparinux. As with low molecular weight heparins, heparinoids are well-known to those skilled in the medical arts.

In addition to therapeutic agents, one or more of the layers disposed on an implantable medical device of this invention may have dispersed within it one or more biobeneficial agents. A biobeneficial agent differs from a therapeutic agent in that a therapeutic agent must be released from a coating layer into the environment to initiate its therapeutic or prophylactic effect while biobeneficial agents have an effect while remaining substantially within, or on, the coating. By "substantially" is meant that, while some of the biobeneficial agent may leak out of a coating, release from the coating is not necessary (although it is not necessarily detrimental) for it to have its beneficial effect. Biobeneficial agents are generally non-toxic, non-antigenic, non-immunogenic substances that enhance the biocompatibility of an implantable medical device by being non-fouling, hemocompatible, actively non-thrombogenic and/or anti-inflammatory.

Representative biobeneficial materials include, but are not limited to, polyethers such as poly(ethylene glycol) (PEG) and poly(propylene glycol); copoly(ether-esters) such as poly (ethylene oxide-co-lactic acid); polyalkylene oxides such as poly(ethylene oxide) and poly(propylene oxide); polyphosphazenes, phosphoryl choline, choline, polymers and co-polymers of hydroxyl bearing monomers such as hydroxyethyl methacrylate, hydroxypropyl methacrylate, hydroxypropylmethacrylamide, poly(ethylene glycol) acrylate, 2-methacryloyloxyethylphosphorylcholine (MPC) and n-vinyl pyrrolidone (VP); carboxylic acid bearing monomers such as methacrylic acid, acrylic acid, alkoxymethacrylate, alkoxyacrylate, and 3-trimethylsilylpropyl methacrylate; polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functionalized poly(vinyl pyrrolidone); biomolecules such as fibrin, fibrinogen, cellulose, starch, collagen, dextran, dextrin, hyaluronic acid, heparin, glycosamino glycan, polysaccharides, elastin, chitosan, alginate, silicones, PolyActive™, and combinations thereof. PolyActive™ refers to a block copolymer of poly(ethylene glycol) and poly(butylene terephthalate).

As used herein, the term "treating" refers to a method of curing or at least alleviating a disease or disorder and/or its attendant symptoms once a patient has contracted the disease or disorder.

As used herein, the term "preventing" refer to a method for barring a patient from acquiring a disease or disorder in the first place or from re-acquiring the disease or disorder after having been treated for it.

As used herein, a "therapeutically effective amount" refers to that amount of a therapeutic agent that elicits the desired biological or medicinal response in a patient that is already exhibiting symptoms of a particular disease or disorder. The response may be, without limitation, delaying the progress of the disease or disorder, alleviating the symptoms of the disease or disorder or eliminating the disease or disorder.

As used herein, a "prophylactically effective amount" refers to an amount that prevents, or delays the onset of, a disease or disorder in the first place. It also refers to an amount that may be less than a therapeutic amount and is administered to a patient after a course or treatment with a therapeutically effective amount has been completed for the purpose of preventing or delaying the recurrence of the disease or disorder.

An aspect of this invention is the use of a very high surface area to volume ratio in the range of 100 mm$^{-1}$ to 1000 mm$^{-1}$. The effect of the large ratio is to increase the area over which surface erosion of the polymeric coating takes place to the point that is exceeds, preferably greatly exceeds, the rate of penetration of degradation-inducing substances such as water, enzymes, acids, etc. into the bulk of the coating. The result is a polymer layer that exhibits the biodegradation characteristics of a surface-eroding polymer even though the polymer is normally characterized as a bulk-eroding polymer. Such polymers include, without limitation, polylactides, polyglycolides and copolymers thereof.

With regard to polylactides and polyglycolides, presently preferred polymers include poly(L-lactide), poly(D-lactide), poly(D,L-lactide), poly(meso-lactide), and copolymers of any of the foregoing with glycolide. Meso-lactide refers to a cyclic lactide prepared from one molecule of L-lactic acid and one molecule of D-lactic acid. While the chemical composition of poly(D,L-lactide) and poly(meso-lactide) are identical, their morphologies are different, with poly(meso-lactide) having no more than two consecutive L- or D-lactic acid-derived units while poly(D,L-lactide) has a statistical distribution of 2, 3, 4 and higher consecutive enantio-identical, that is L or D, lactic acid-derived units.

In addition to employing a high surface area to volume ratio, a relatively low average molecular weight polymer is presently preferred. A number average molecular weight of from about 20 kDA to about 600 kDA, preferably about 40 kDA to about 200 kDa and most preferably at present from about 50 kDA to about 100 kDA may be used. Without being held to any particular theory, it is believed that use of low molecular weight polymers reduces the lag time to mass release.

It is also desirable to use a high therapeutic substance to polymer ratio in the reservoir layer of this invention. A drug-to-polymer wt/wt ratio of from about 1:5 to about 5:1 may be employed. Preferably the range is from about 1:2 to 2:1 and most preferably at present a ratio of about 1:1 may be used. These ranges, together with the above surface area to volume ratios and polymer molecular weights, permit a broad range of release rates and therefore release profiles to be achieved, the range being substantially greater than those normally described for such bulk-eroding polymers in the art, particularly with regard to hydrophobic therapeutic agents.

It is also presently preferred that the polymer be substantially amorphous. If the polymer is two phase, that is, if it contains substantial crystalline as well as amorphous regions, surface erosion can result in the release of large crystalline particles which may migrate to regions of the vasculature comprising smaller diameter vessels such as capillaries where they may lodge and cause serious side effects. "Substantially amorphous" refers to a polymer that is less than 10% crystalline, preferably less than 5% crystalline and presently most preferably less than 1% crystalline. A substantially amorphous polymer as used herein has the further characteristic of not releasing large crystalline particles as it erodes.

Using the above parameters, lactide polymer layers having degradation characteristics substantially different from those normally observed may be obtained. For example, the literature reports absorption of a poly(L-lactide)-based system of about 50% in 12-24 months and absorption of a poly(D,L-lactide)-based system of about 50% in 6-9 months, depending on the geometry of the construct. However, a poly(D,L-lactide)-based system of the current invention has exhibited a 60-70% absorption at 180 days, substantially different from that previously reported. Moreover, the polymer mass loss in the system of the current invention was approximately linear, which would be expected of a surface-eroding polymer. Furthermore, the mass loss occurs before the average molecular weight of the fragmenting polymer has been reduced to the level suggested in the literature for mass loss in a bulk-eroding polymer. Thus, by using the aspects of this invention, it is clear that normally bulk-eroding polymers such as, without limitation, polylactide, polyglycolide and copolymers thereof, can be used as reservoir layers for implantable medical devices and will exhibit biodegradation characteristics that are or very closely approximate surface erosion characteristics.

EXAMPLE 1

A 14 mm, 6 crest stainless steel S-Stent is coated with 2 microns of PARYLENE C®. Onto this is applied 400 μg of a 1:1 mixture of everolimus in poly(D,L-lactide) as a 9% w/w total solids solution in acetone. Coating is accomplished using a syringe, which results in a coating covering the entire abluminal surfaces and approximately half of the side-wall surface area. The acetone is removed by placing the stent in a vacuum oven at −28 inches of mercury for 4 hours at approximately 30° C. The result is a stent having an average coating thickness of 7 microns and a surface area to volume ratio of 140 mm$^{-1}$.

EXAMPLE 2

A film, 20 microns thick, is formed by solution coating of a 1:2 mixture of rapamycin and poly(D,L-lactide-co-glycolide) as a 20% w/w total solids solution in acetone onto a flexible substrate. After removing the acetone by baking at 60° C. for one hour, the coated substrate is cut into strips 2 mm wide and the polymeric strips are removed from the substrate. The resulting strips have a surface area to volume ratio of approximately 100 mm$^{-1}$. The strips are wrapped around the anastomosis of vascular grafts used for dialysis to reduce an astomotic proliferation.

What is claimed:

1. An implantable medical device, comprising:
a polymer layer comprising a biocompatible biodegradable polymer wherein the polymer layer is disposed over a surface of the medical device at a surface area to volume ratio of from about 100 mm$^{-1}$ to about 1000 mm$^{-1}$; and,
a therapeutic agent dispersed in the polymer layer at a drug/polymer wt/wt ratio of from about 1:5 to about 5:1.

2. The device of claim 1, wherein the surface is an outer surface and optionally all or part of an edge surface.

3. The device of claim 1, wherein the surface is a luminal surface and optionally all or part of an edge surface.

4. The implantable medical device of claim 1, wherein the polymer layer has a surface area to volume ratio of from about 100 mm$^{-1}$ to about 500 mm$^{-1}$.

5. The implantable medical device of claim 1, wherein the polymer layer has a surface area to volume ratio of from about 100 mm$^{-1}$ to about 250 mm$^{-1}$.

6. The implantable medical device of claim 1, wherein the drug/polymer wt/wt ratio is from about 1:2 to 2:1.

7. The implantable medical device of claim 1, wherein the drug/polymer wt/wt ratio is about 1:1.

8. The implantable medical device of claim 1, wherein the biocompatible biodegradable polymer is selected from the group consisting of poly(L-lactide), poly(D-lactide), poly(D,L-lactide), poly(meso-lactide), polyglycolide, poly(L-lactide-co-D, L-lactide), poly(L-lactide-co-glycolide), poly(D-lactide-co-glycolide), poly(D,L-lactide-co-glycolide), poly(meso-lactide-co-glycolide), poly(caprolactone), poly(hydroxyvalerate), poly(hydroxybutyrate), poly (ester amide), and poly(ethylene glycol-co-butylene terephthalate) (POLYACTIVE®).

9. The implantable medical device of claim 1, wherein the biocompatible biodegradable polymer has a molecular weight of from about 20 to about 600 kDaltons.

10. The implantable medical device of claim 1, wherein the biocompatible biodegradable polymer has as molecular weight of from about 40 to about 200 kDaltons.

11. The implantable medical device of claim 1, wherein the biocompatible biodegradable polymer has as molecular weight of from about 50 to about 100 kDaltons.

12. The implantable medical device of claim 8, wherein the biocompatible biodegradable polymer has a molecular weight of from about 20 to about 600 kDaltons.

13. The implantable medical device of claim 8, wherein the biocompatible biodegradable polymer has a molecular weight of from about 40 to about 200 kDaltons.

14. The implantable medical device of claim 8, wherein the biocompatible biodegradable polymer has as molecular weight of from about 50 to about 100 kDaltons 15. The implantable medical device of claim 1, wherein the biocompatible biodegradable polymer is substantially amorphous.

16. The implantable medical device of claim 15, wherein the biocompatible biodegradable polymer is selected from the group consisting of poly(D,L-lactide), poly(meso-lactide), poly(L-lactide-co-D,L-lactide), poly(L-lactide-co-glycolide), poly(D,L-lactide-co-glycoide), poly(D-lactide-co-glycolide) and poly(meso-lactide-co-glycolide).

17. The implantable medical device of claim 1, wherein the therapeutic agent is selected from the group consisting of actinomycin D, paclitaxel, docetaxel, methotrexate, azathioprine, vincristine, vinblastine, fluorouracil, doxorubicin hydrochloride, mitomycin, sodium heparin, low molecular weight heparins, heparinoids, heparin derivatives having hydrophobic counter ions, hirudin, argatroban, forskolin, vapiprost, prostacyclin, dextran, D-phe-pro-arg-chloromethylketone, dipyridamole, glycoprotein IIb/IIIa platelet membrane receptor antagonist antibody, recombinant hirudin, and thrombin, angiopeptin, captopril, cilazapril, lisinopril, nifedipine, colchicine, fibroblast growth factor (FGF) antagonists, fish oil (ù-3- fatty acid), histamine antagonists, lovastatin, monoclonal antibodies, nitroprusside, phosphodiesterase inhibitors, prostaglandin inhibitors, suramin, serotonin blockers, steroids, thioprotease inhibitors, triazolopyrimidine, nitric oxide, permirolast potassium, alpha-interferon, genetically engineered epithelial cells, rapamycin, everolimus, dexamethasone and 17-allylamino-17-demethoxygeldanamycin.

18. The implantable medical device of claim 1, wherein the therapeutic agent is an antiproliferative agent.

19. The implantable medical device of claim 18, wherein the therapeutic agent is everolimus.

20. The implantable medical device of claim 1, further comprising a primer layer applied onto the surface of the device between the surface and the polymer layer.

21. The implantable medical device of claim 20, wherein the primer layer comprises a polymer selected from the group consisting of poly(monochloro-paraxylylene) (PARYLENE C®), polyacrylate, polymethacrylate, poly(D,L-lactide), poly(L-lactide), poly (L-lactide-co-glycolide), poly(meso-lactide), poly(meso-lactide-co-glycolide), poly(D,L-lactide-co-glycolide), poly(caprolactone), poly(hydroxyvalerate) poly(hydroxybutyrate) and poly(ethylene glycol-co-butylene terephthalate) (POLYACTIVE®).

22. The implantable medical device of claim 21, wherein the primer layer comprises a polymer selected from the group consisting of poly(n-butyl methacrylate) and PARYLENE C®.

23. A method of treating a vascular disease comprising:
deploying to a site in the vasculature of a patient in need thereof an implantable medical device comprising a biocompatible biodegradable polymer layer disposed over a surface thereof such that the surface area to volume ratio is from about 100 mm$^{-1}$ to about 1000 mm$^{-1}$, the polymer layer further comprising a therapeutic agent in a drug/polymer wt/wt ratio of from about 1:5 to about 5:1; and, releasing the implantable medical device at the site.

24. The method of claim 23, wherein deploying comprises using a catheter.

25. The method of claim 23, wherein the drug/polymer wt/wt ratio is from about 1:2 to about 2:1.

26. The method of claim 23, wherein the drug/polymer wt/wt ratio is about 1:1.

27. The method of claim 23, wherein the biocompatible biodegradable polymer has a number average molecular weight of from about 20 kDa to about 600 kDa.

28. The method of claim 23, wherein the biocompatible biodegradable polymer has a number average molecular weight of from about 40 kDa to about 200 kDa.

29. The method of claim 23, wherein the number average molecular weight is from about 50 kDa to about 100 kDa.

30. The method of claim 23, wherein the biocompatible biodegradable polymer is selected from the group consisting of poly(L-lactide), poly(D-lactide), poly(D,L-lactide), poly(L-lactide-co-D,L-lactide), poly(meso-lactide), polyglycolide, poly(L-lactide-co-glycolide), poly(D-lactide-co-glycolide), poly(D,L-lactide-co-glycolide), poly(meso-lactide-co-glycolide), poly(caprolactone), poly(hydroxyvalerate), poly(hydroxybutyrate), poly(ethylene glycol-co-butylene terephthalate) (POLYACTIVE®), and poly(ester amide).

31. The method of claim 23, wherein the biocompatible biodegradable polymer is substantially amorphous.

32. The method of claim 31, wherein the biocompatible biodegradable polymer is selected from the group consisting of poly(D,L-lactide), poly(meso-lactide), poly(L-lactide-co-glycolide), poly(D,Llactide-co-glycolide), poly (D-lactide-co-glycolide) and poly(meso-lactide-co-glycolide).

33. The method of claim 23, wherein the vascular disease is restenosis.

34. The method of claim 23, wherein the vascular disease is vulnerable plaque.

35. The method of claim 33, wherein the therapeutic agent is selected from the group consisting of everolimus and 17-allylamino-17-demethoxy-geldanamycin.

36. The method of claim 34, wherein the therapeutic agent is selected from the group consisting of everolimus and 17-allylamino-17-demethoxy-geldanamycin.

* * * * *